US010130338B2

(12) United States Patent
Chaggares et al.

(10) Patent No.: US 10,130,338 B2
(45) Date of Patent: *Nov. 20, 2018

(54) ULTRASOUND PROBE AND ALIGNED NEEDLE GUIDE SYSTEM

(71) Applicant: FUJIFILM SonoSite, Inc., Bothell, WA (US)

(72) Inventors: N. Chris Chaggares, Whitby (CA); Eric Michael Rieder, Georgetown (CA)

(73) Assignee: FUJIFILM SonoSite, Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/866,069

(22) Filed: Jan. 9, 2018

(65) Prior Publication Data

US 2018/0125453 A1   May 10, 2018

Related U.S. Application Data

(63) Continuation of application No. 15/602,026, filed on May 22, 2017, which is a continuation of application
(Continued)

(51) Int. Cl.
*A61B 8/00* (2006.01)
*A61B 10/02* (2006.01)
(Continued)

(52) U.S. Cl.
CPC .......... *A61B 8/4455* (2013.01); *A61B 8/0841* (2013.01); *A61B 8/12* (2013.01);
(Continued)

(58) Field of Classification Search
CPC . A61B 10/02; A61B 10/0241; A61B 10/0275; A61B 17/3403; A61B 2010/045;
(Continued)

(56) References Cited

U.S. PATENT DOCUMENTS 5,235,987 A    8/1993  Wolfe et al.
5,437,283 A    8/1995  Ranalletta et al.
(Continued)

FOREIGN PATENT DOCUMENTS

CN    1575776 A    2/2005
EP    0955010 A1   11/1999
(Continued)

OTHER PUBLICATIONS

Japanese Patent Office, First Office Action, JP Patent Application 2017-169532, dated Oct. 24, 2017, 10 pages, with English translation.
(Continued)

*Primary Examiner* — Michael Rozanski
(74) *Attorney, Agent, or Firm* — Perkins Coie LLP

(57) ABSTRACT

A side-fire ultrasonic probe includes an alignment feature that, when used to connect the probe with a needle guide for intra-cavity medical procedures, enables alignment of a needle in an imaging plane of an ultrasonic transducer. The alignment feature is configured such that alignment of the needle within the imaging plane is accomplished when a protective sheath is disposed between the alignment feature and the needle guide. This configuration can be used with high frequency ultrasonic arrays having frequency distributions centered at about 20 MHz, and for medical procedures, such as biopsying organs or other bodily intra-cavity structures, and delivering intra-cavity therapies.

13 Claims, 3 Drawing Sheets

Related U.S. Application Data

No. 14/746,633, filed on Jun. 22, 2015, now Pat. No. 9,655,591, which is a continuation of application No. 13/545,352, filed on Jul. 10, 2012, now Pat. No. 9,113,825.

(51) Int. Cl.

| | | |
|---|---|---|
| *A61B 8/12* | (2006.01) | |
| *A61B 8/08* | (2006.01) | |
| *A61B 17/34* | (2006.01) | |
| *A61B 10/04* | (2006.01) | |
| *A61B 17/00* | (2006.01) | |

(52) U.S. Cl.
CPC .......... *A61B 8/4422* (2013.01); *A61B 8/4494* (2013.01); *A61B 10/02* (2013.01); *A61B 10/0241* (2013.01); *A61B 10/0275* (2013.01); *A61B 17/3403* (2013.01); *A61B 8/445* (2013.01); *A61B 8/4444* (2013.01); *A61B 2010/045* (2013.01); *A61B 2017/00274* (2013.01); *A61B 2017/3413* (2013.01)

(58) Field of Classification Search
CPC . A61B 2017/3413; A61B 8/0841; A61B 8/12; A61B 8/4422; A61B 8/4444; A61B 8/445; A61B 8/4455; A61B 8/4494
See application file for complete search history.

(56) References Cited

U.S. PATENT DOCUMENTS

| | | |
|---|---|---|
| 6,261,234 B1 | 7/2001 | Lin |
| 6,443,902 B1 | 9/2002 | Sasady |
| 7,691,066 B2 | 4/2010 | Kosaku |
| 7,750,536 B2 | 7/2010 | Chaggares et al. |
| 9,113,825 B2 | 8/2015 | Chaggares et al. |
| 9,655,591 B2 | 5/2017 | Chaggares et al. |
| 2006/0184034 A1 | 8/2006 | Haim et al. |
| 2007/0129632 A1 | 6/2007 | Voie et al. |
| 2007/0232924 A1 | 10/2007 | Karasawa et al. |
| 2009/0099544 A1 | 4/2009 | Munrow et al. |
| 2009/0131790 A1 | 5/2009 | Munrow et al. |
| 2014/0018667 A1 | 1/2014 | Chaggares et al. |
| 2016/0038118 A1 | 2/2016 | Chaggares et al. |

FOREIGN PATENT DOCUMENTS

| | | |
|---|---|---|
| JP | 58-7230 | 1/1983 |
| JP | 58-7230 | 10/1985 |
| JP | 02071732 A | 3/1990 |
| JP | 4-77908 | 7/1992 |
| JP | 09201360 A | 8/1997 |
| JP | 10028687 A | 2/1998 |
| JP | 2000201936 A | 7/2000 |
| JP | 2001500026 A | 1/2001 |
| JP | 2001120550 A | 5/2001 |
| JP | 2-120379 | 4/2002 |
| JP | 2003299654 A | 10/2003 |
| JP | 4-77908 | 3/2004 |
| JP | 2005034273 A | 2/2005 |
| JP | 2006506128 A | 2/2006 |
| JP | 2006212166 A | 8/2006 |
| JP | 2007-244415 | 9/2007 |
| JP | 2007244415 A | 9/2007 |
| JP | 2007289693 A | 11/2007 |
| JP | 2008253647 A | 10/2008 |
| JP | 2011500164 A | 1/2011 |
| JP | 2011505206 A | 2/2011 |
| JP | 2015521932 A | 8/2015 |
| WO | 2007124265 A2 | 11/2007 |
| WO | 2007124265 A3 | 1/2008 |
| WO | 2014009810 | 1/2014 |

OTHER PUBLICATIONS

Canadian Intellectual Property Office, Examiner's Report, CA Patent Application 2,878,789, dated Aug. 11, 2016, 4 pages.
European Patent Office, Extended European Search Report, EP Patent Application 13816371.2, dated Feb. 9, 2016, 10 pages.
International Searching Authority, International Search Report and Written Opinion; PCT Application PCT/IB2013/001979, dated Jan. 22, 2014, 9 pages.
Japanese Patent Office, Official Action, JP Patent Application 2015-521082, dated Aug. 8, 2016, 12 pages; includes English translation.
Krieger, Axel et al. "Design of a Novel MRI Compatible Manipulator for Image Guided Prostate Interventions." IEEE Transactions on Biomedical Engineering, vol. 52, No. 2, Feb. 2005, pp. 306-313.
State Intellectual Property Office of China, First Office Action, CN Patent Application 201380046978.5, dated Jul. 26, 2016, 10 pages.
Yacoub, Joseph H. et al. "Imaging-guided Prostate Biopsy: Conventional and Emerging Techniques." RadioGraphics 2012, vol. 32, No. 3, pp. 819-838.
European Patent Office, Intention to Grant, EP Application 13816371. 2, dated Oct. 13, 2017, 24 pages.

ULTRASOUND PROBE AND ALIGNED NEEDLE GUIDE SYSTEM

CROSS-REFERENCE TO RELATED APPLICATIONS

This application is a continuation of U.S. patent application Ser. No. 15/602,026, filed May 22, 2017, which is a continuation of U.S. patent application Ser. No. 14/746,633 filed Jun. 22, 2015, now U.S. Pat. No. 9,655,591; which is a continuation of U.S. patent application Ser. No. 13/545,352 filed Jul. 10, 2012, now U.S. Pat. No. 9,113,825; which are hereby incorporated by reference in their entireties.

BACKGROUND

The present disclosure relates generally to medical imaging and diagnostics, and more specifically to an ultrasonic probe and an aligned needle guide system.

Accessing organs and structures of the human body through body cavities is a standard medical technique. In some procedures, diagnostic tools are inserted into a body cavity to examine or biopsy an organ or other body structure. The information collected is then used for the detection and evaluation of a wide variety of medical conditions. In particular, ultrasonic devices are used to identify intra-cavity structures, such a prostate, by transmitting and receiving ultrasonic waves. The received waves are transformed into an image of the intra-cavity structure, which can then be used to navigate a biopsy needle to a desired location within the image.

Ultrasonic transducers used in these medical applications are typically encased within an anatomically compatible housing to improve patient comfort during insertion into the patient. Ultrasonic transducer housings fall into one of two broad configuration types: "end-fire" and "side-fire." The end-fire type transmits ultrasonic waves from a tip of the housing, whereas the side-fire type transmits from a sidewall of the housing. Regardless of the housing type, the ultrasonic image can be used to navigate a biopsy needle to an exterior surface of an intra-cavity bodily structure.

SUMMARY

In one embodiment, an ultrasonic probe of the present disclosure includes a cylindrical housing that includes a needle guide alignment feature on the surface of the housing. The alignment feature is used to connect a needle guide to the cylindrical housing and to align the needle guide such that a needle translated through the guide is translated in an imaging plane of the ultrasonic transducer. The alignment feature is configured such that the needle is aligned in the imaging plane even when a protective sheath is disposed between the housing and the needle guide. The protective sheath may facilitate sanitation, sterilization, and re-use of the probe.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Overview

Embodiments described herein include a side-fire ultrasonic probe with an alignment feature that, when used to connect the probe to a needle guide for intra-cavity medical procedures (e.g., biopsying organs or other bodily intra-cavity structures, delivering intra-cavity therapies), facilitates alignment of one or more needles translated through the needle guide with an imaging plane of an ultrasonic transducer. The alignment feature is configured such that alignment of a needle within the imaging plane is accomplished even when a protective sheath is disposed between the alignment feature and the needle guide.

By positioning the translated needles within the imaging plane of a side-fire type ultrasonic probe, an ultrasonic image can be used to image an advancing needle with respect to an intra-cavity structure of interest. This ability is particularly useful when the ultrasonic transducer has a frequency and/or resolution sufficient to image intra-structure or intra-organ features. Simultaneously imaging the structure of interest and the needle permits navigation of the needle to a specific intra-cavity structure within a human body, or, given sufficient resolution of the ultrasonic transducer, navigation of the needle to a specific location within the structure. This can then improve the diagnostic capability of the procedure or effectiveness of the therapy. Allowing for positioning of a needle oriented at different angles with respect to the probe enables access to a range of locations within the body or structure by the needles while reducing the manipulation of the probe. This can improve patient comfort during the procedure, as well as patient safety.

Ultrasonic Probe and Aligned Needle Assembly

Figure 1:
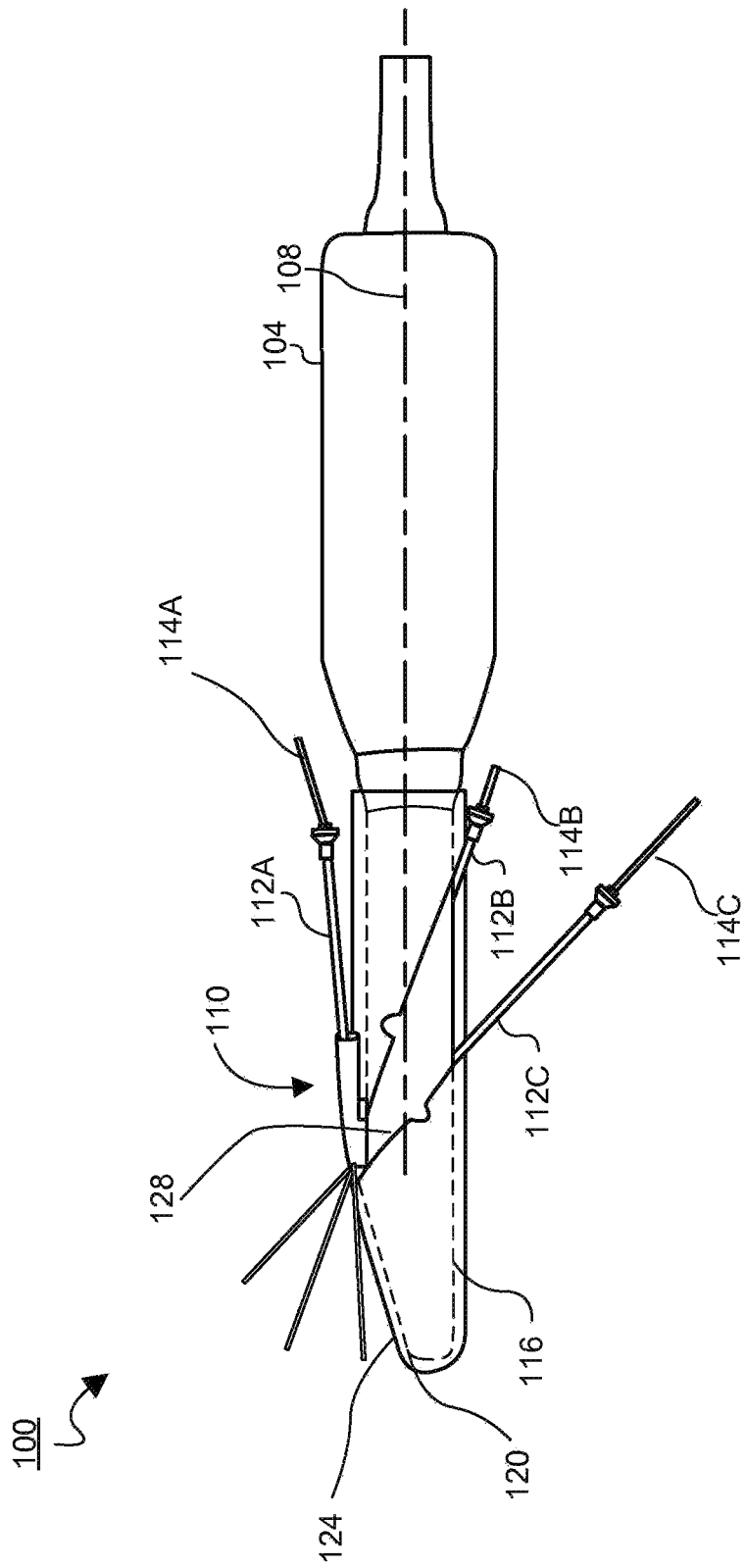
FIG. 1 illustrates an example of an ultrasonic probe with an aligned needle guide, in an embodiment.

FIG. 1 illustrates an embodiment of a side-fire ultrasonic probe assembly 100 having an alignment feature that enables alignment of a needle guide 110 such that needles (e.g., any of needles 114A-C, "114" for brevity) translated through the guide are translated into an imaging plane produced by the ultrasonic transducer array. The imaging plane is defined by a pathway of ultrasonic waves produced by the ultrasonic transducer. The ultrasonic probe assembly 100 includes a cylindrical housing 104 having a longitudinal axis 108, and a transducer housing 116 having an angled face 120. The transducer housing 116 encloses an ultrasonic transducer array used for the production of ultrasonic waves, the reflections of which are transformed into images. A protective sheath 124, disposed between the cylindrical housing 104 and the needle guide 110, covers a portion of the cylindrical housing and the transducer housing 116. The ultrasonic probe assembly 100 also includes a needle assembly alignment feature 128, shown in more detail in FIGS. 2 and 3.

The cylindrical housing 104 of the ultrasonic probe assembly 100 has a number of uses including, but not limited to, enclosing wiring and/or electronic components used to operate the ultrasonic transducer, providing a structure with which to connect other elements of the assembly (e.g., the needle guide 110), and providing a proximal end (i.e., a handle) used by an operator for manipulating the assembly. In this example, the cylindrical housing 104 has a circular or elliptical cross-section that is ergonomically insertable into a body cavity, such as a rectum, to image, biopsy, and/or deliver a therapy to a body structure of interest, such as a prostate. While other embodiments of the cylindrical housing 104 are not limited to cylinders or circular or elliptical cross-sections, housings having points or edges may cause patient discomfort or damage sensitive tissue. The longitudinal axis 108 of the cylindrical housing 104 is parallel to the long axis of the cylindrical housing and is used as a convenient reference when describing other features of the embodiments.

The needle guide 110, which includes individual guide channels 112A-C ("112" collectively), into which one or more of the needles 114 can be inserted, is attached to the cylindrical housing 104 over the protective sheath 124 using the alignment feature 128. The details of the needle guide 110 are described in more detail in the context of FIGS. 2 and 3.

One needle of the needles 114 is used to biopsy intra-cavity structures of interest, such as a prostate (shown in FIG. 1 by an ellipse), by being translated through one channel 112 of the needle guide 110, through port 113 (shown in FIGS. 2 and 3), and into the ultrasonic imaging plane. The three channels 112 are oriented at different angles with respect to the horizontal axis 108 of the probe assembly 100 so that different locations within the body structure can be accessed by a needle 114 without moving the probe within the patient. Because both the needle (e.g., needle 114A) and the structure of interest are in the imaging plane simultaneously, and therefore both imaged using reflected ultrasonic waves, the needle can be navigated to a specific location of interest. This location can be on the surface of the body structure or, provided that the ultrasonic transducer is capable of intra-structure resolution (typically achieved at high transducer frequencies of approximately 20 MHz), even within a specific body structure.

The transducer housing 116 is located at the distal end of the cylindrical housing 104. The transducer housing 116 substantially surrounds the ultrasonic transducer used to produce ultrasonic waves. In this example, the transducer housing 116 is ergonomically shaped to improve patient comfort during insertion of the assembly 100 into a body cavity. This ergonomic shape can also improve patient comfort during operation of the assembly 100 for imaging and biopsying intra-cavity body structures.

In this example, because the ultrasonic transducer transmits ultrasonic waves through a sidewall of the cylindrical housing 104, the design of the assembly 100 is sometimes referred to as a "side-fire" design. Other embodiments of the invention may be used with "end-fire" designs, in which the ultrasonic waves are transmitted from a terminal end of the transducer housing 116 (i.e., in a direction generally parallel to the longitudinal axis 108).

The transducer housed by the transducer housing 116 may comprise an array of piezoelectric elements that produce ultrasonic waves when electrically actuated. In some examples, the transducer array can produce ultrasonic waves having a frequency distribution centered between approximately 1 MHz and 12 MHz. The resolution of images produced at these lower frequencies may be sufficient to discern the outline and/or outer surfaces of intra-cavity body structures. In other examples, the transducer array can produce ultrasonic waves having a frequency distribution centered at approximately 20 MHz and a 6 dB corner frequency of approximately 27 MHz. The resolution of images produced at these higher frequencies may be sufficient to image structures within the intra-cavity body structures (i.e., intra-organ resolution). This higher resolution and imaging facilitates navigation of the needles 114A-C to locations within the body structure, which can then be biopsied. Also, because the interior of the organ or body structure can be imaged, this resolution can also help prevent accidental damage to the body structure.

The above description of the approximate center of the frequency distribution is important due to inconsistent description of transducer operating frequency in the art: while some artisans describe operating frequency by citing the center of the frequency distribution, other artisans describe operating frequency by citing the upper limit of the distribution.

The side-fire design of the transducer housing 116 includes the angled face 120, which facilitates acoustic coupling between the transducer and the body structure to be imaged. By matching the angle of the angled face 120 to the shape of the body structure, the transducer and thus the ultrasonic waves used to image the body structure are brought proximate to a surface of the body structure without angling the assembly 100 as a whole. This improves the quality of the image and comfort of the patient by reducing the manipulation of the probe 100 needed to acquire an image. In some embodiments, the angled face 120 is angled about 13° to match a typical slope of a prostate surface. In other embodiments, the angled face 120 is angled at least 5°. In further embodiments, this angle can be varied depending on the natural angle (or range of natural angles) of the body structure surface to be imaged. In still further embodiments, the transducer housing 116 does not have an angled face, but rather is a standard side-fire design.

In the example shown, the protective sheath 124 covers the transducer housing 116, and at least a portion of the cylindrical portion 104. Acting as a barrier, the protective sheath 124 prevents body fluids or other substances from contaminating the assembly 100. By limiting access of body fluids and contaminants to the interior and exterior of the assembly 100, the protective sheath 124 facilitates sanitation, sterilization, and re-use of the assembly.

In some examples, the protective sheath 124 is designed to match the shape of the assembly 100, including the cylindrical housing 104, the transducer housing 116, the angled face 120, and the alignment feature 128. In other examples, the protective sheath 124 is designed to match the shape of conventional ultrasonic probe assemblies and not is customized to match the shape of the assembly 100. In some examples, the protective sheath 124 is made from a polymer, although other materials that permit the transmission and reception of ultrasonic waves can be used.

Needle Alignment

The alignment feature 128 is configured such that a 114 is aligned with and disposed in the imaging plane (shown in FIG. 2) when the needle guide 110 is engaged with the alignment feature through the protective sheath 124 and the needle has been translated through one of the channels 112 of the needle guide and through the port 113 into the imaging plane. In some embodiments, the alignment feature 128 is a negative feature imprinted, molded, or embossed into the surface of cylindrical housing 104 and configured to mate with an approximately matching positive feature on the needle guide 110. This negative profile enables the needle guide 110 to connect to the cylindrical housing 104, enabling the imaging of a needle 114 during a procedure, as described above, while also maintaining an anatomically compatible profile. In other embodiments, the alignment feature 128 is a positive feature attached, connected, or integrated onto the surface the cylindrical housing 104. In still other embodiments, the alignment feature 128 is a combination of positive and negative features.

In some examples, the alignment feature 128 is designed to connect the needle guide 110 to the cylindrical housing 104 and maintain alignment of the needles 114 in the ultrasonic imaging plane when the protective sheath 124 is disposed between the cylindrical housing and the needle assembly. In some embodiments of this example, the alignment feature 128 can be adjusted to accommodate thickness variations of the protective sheath 124, thereby maintaining alignment of the needle 114 in the imaging plane regardless of sheath thickness. In other examples, the alignment feature 128 is designed to maintain alignment between the needle 114 and the imaging plane without adjustment and regardless of the thickness of the protective sheath 124.

Figure 2:
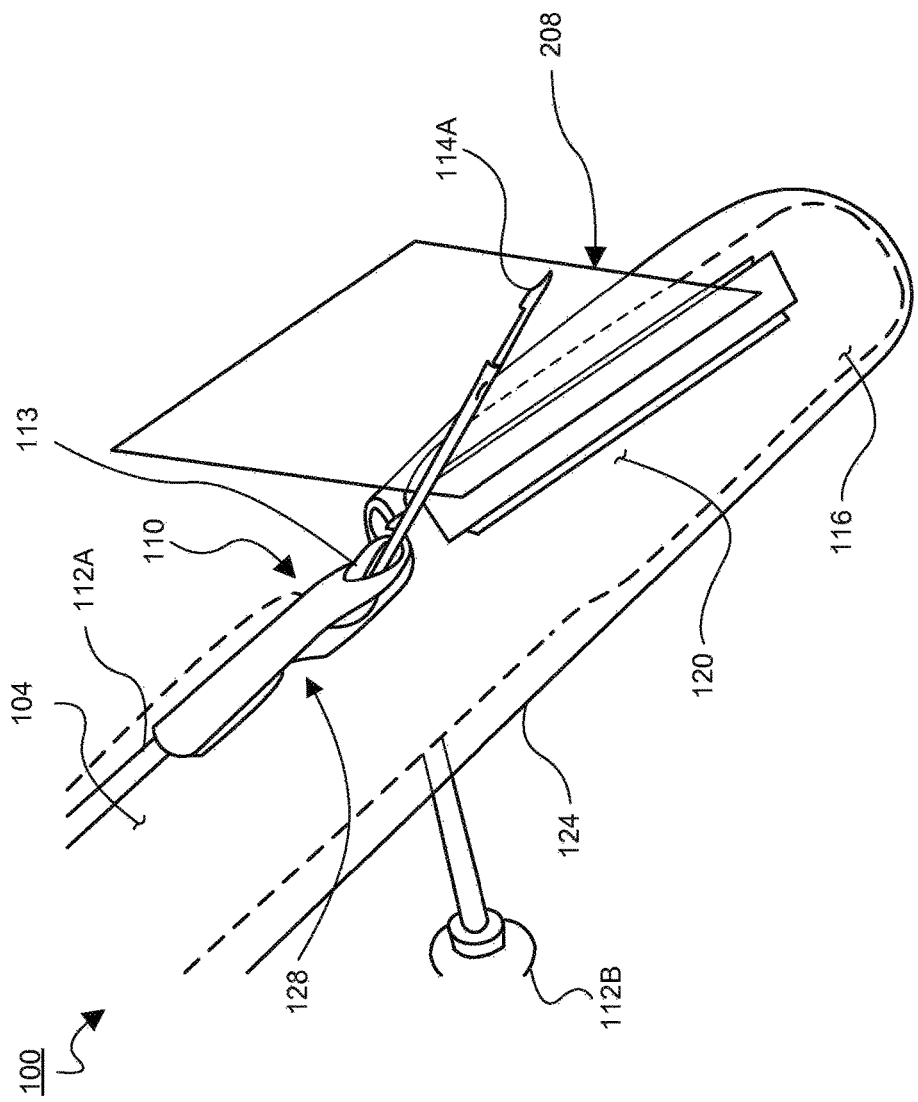
FIG. 2 is a perspective view of a tip of an ultrasonic probe, wherein the probe is encased in a protective sheath and, using a needle guide, a needle is aligned in an imaging plane produced by an ultrasonic transducer, the alignment facilitated by an alignment feature disposed on the housing, in an embodiment.

FIG. 2 illustrates the alignment of the needle 114A in the acoustic imaging plane of the ultrasonic probe assembly 100, as discussed above. This figure depicts a portion of the needle guide 110, the alignment feature 128, the needle 114A, and an acoustic imaging plane 208. As will be appreciated, the needle 114A is selected only for convenience. Embodiments of the present disclosure are applicable to the needles 114B and 114C, which can be translated through the corresponding needle guide channels 112 and emerge from port 113 at different angles with respect to the horizontal axis 108 of the probe 100 into the imaging plane 208. Also shown in FIG. 2 are portions of the cylindrical housing 104, the transducer housing 116, the angled face 120, and the protective sheath 124.

In the example shown, the cylindrical housing 104 and the transducer housing 116 are protected by the protective sheath 124. The needle guide 110 is disposed in the alignment feature 128, in this example a negative feature on the surface of the cylindrical housing 104, thereby compressing the protective sheath 124 into the alignment feature.

As shown, the needle guide 110, the needle 114A, the alignment feature 128, the protective sheath 124, and the transducer are configured such that the needle is disposed within the imaging plane 208 when extended distally through the needle guide 110. As mentioned above, this enables the needle 114A to be viewed during use and, in particular, enables the needle to be navigated to the body structure of interest. Furthermore, for examples of the ultrasonic probe assembly 100 using a transducer having frequencies centered at approximately 20 MHz, the needle 114A can be navigated to intra-organ features, thereby enabling precision biopsy or treatment of specific intra-organ areas.

In one aspect, this alignment of the needle 114A and the image plane 208 is accomplished by configuring the needle guide 110, a needle 114, and the alignment feature 128 such that the needle is positioned in the imaging plane 208 at a location in the imaging plane that is a function of how far the needle is translated. This alignment is further accomplished by controlling the dimensional tolerances of the various components to a total of approximately half of the width of the imaging plane 208. Controlling the total dimensional variation to only a portion of the width of the imaging plane permits some dimensional and/or alignment variation in the various components while still enabling the needle 114A to be translated into the imaging plane 208.

In one embodiment of the above example, ultrasonic transducers having a frequency distribution centered at about 20 MHz produce an imaging plane from approximately 300 microns to approximately 500 microns wide. By configuring the various components (e.g., the housing 104, the alignment feature 128, the needle guide 110, and the protective sheath 124) described above, and controlling the combined dimensional variation of these components to approximately 250 microns, the needle 114A can be reliably imaged during and after its translation into the imaging plane 208.

In examples in which the diameter of the needle 114A is larger than the imaging plane 208 (e.g., a needle approximately 1000 microns in diameter used with an imaging plane approximately 500 microns wide), the entire diameter of the needle need not be in the imaging plane to image the needle and navigate it to a body structure location. Rather, a section that includes the needle point can be used to navigate the needle safely to, and into, the structure.

Needle Guide

Figure 3:
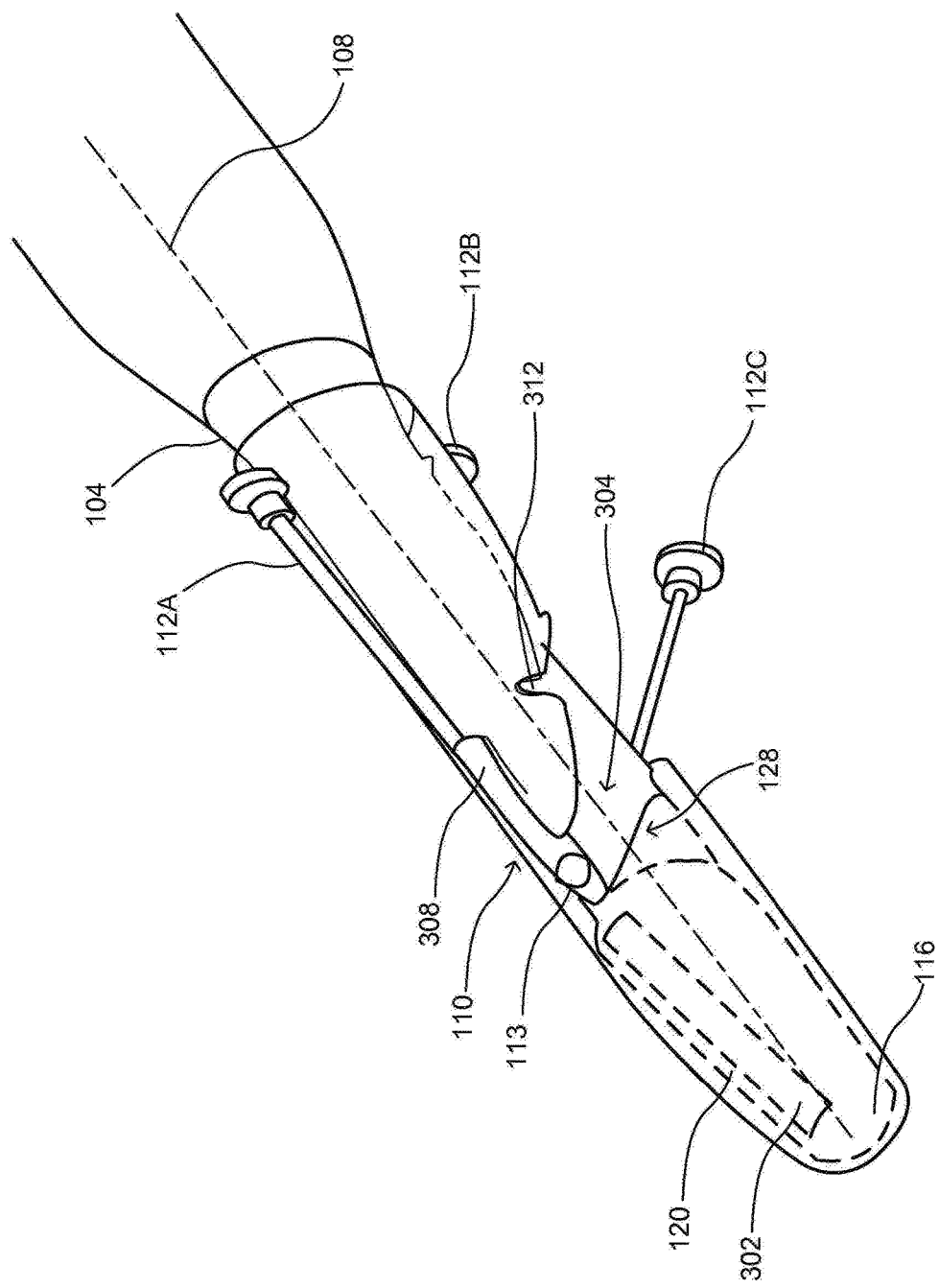
FIG. 3 is perspective view of an ultrasonic probe covered by a protective sheath and an attached needle guide aligned with the probe, in an embodiment.

FIG. 3 illustrates an ultrasonic probe 300 that includes an ultrasonic transducer 302, and the needle guide 110 attached to the cylindrical housing 104 over the protective sheath 124 using the alignment feature 128. In this example, the needle guide 110 includes the channels 112A-C, the port 113, a frame 304, a needle housing 308, and a positioning feature 312.

In this example, the three needles 114A-C are shown in each of the three channels 112A-C of the needle guide 110 to illustrate the different angles at which the channels are oriented with respect to the longitudinal axis 108 of the housing 104. This diversity of angles is used to increase the range of locations within the body accessible by the needles while minimizing the manipulation required of the assembly 100 needed to access these locations. Because the needles 114 in the channels 112 of the needle guide 110 are positioned at different angles (and can exit port 113 at different angles), they each can be inserted into a different location in the body without articulating, twisting, translating, or otherwise moving the assembly 100 (as illustrated in FIG. 1). Furthermore, the multiple channels 112 of the needle guide 110 (not limited to only the three shown) permit multiple biopsy needles to take samples from different locations within a body structure without additional movement of the assembly 100. This arrangement improves patient comfort during a procedure requiring the collection of biopsy samples, or the delivery of a therapy, to multiple locations within the body.

The angles of the channels in the needle guide 110 (and therefore needles 114) are determined, in part, by the locations within the body or body structure intended to be biopsied, and the depth of penetration into a body cavity by the assembly 100 that is needed to access the body structure of interest. Other factors used to determine these angles may include the ability to access a wide range of locations within the body cavity, and the need to maintain the position and/or alignment of the needles within the imaging plane of the transducer (as shown in FIG. 2). In some embodiments, the channels of the needle guide 110 and the needles 114 can also be angled to limit or prevent access to particularly delicate or sensitive body structures near the structure of interest (e.g., a nerve bundle near the sphincter during a prostate biopsy). For example, the needles can be arranged at angles from −5° (i.e., 5° below the horizontal axis), up to about 30°, although any practical angle can be used.

In one example, because the needle 114C is inserted into the channel 112 of the needle guide 110 that has a greater angle with respect to the longitudinal axis 108 than the portion of the needle guide used with needle 114A (which is substantially parallel to the longitudinal axis), the locations accessible by these two needles are different. Therefore, different regions of a body structure can be biopsied without manipulation of the assembly 100 as a whole. In one example, an angle of a needle is selected to prevent a needle from accidental insertion into a sphincter nerve bundle proximate to the rectum and prostate. As mentioned above, regardless of the angle of the needles 114, the needle guide 110 and the protective sheath 124 are arranged such that the needles are translated into the imaging plane of the ultrasonic transducer.

The frame 304 of the needle guide 110 is used to connect one or more of the needles 114 to the needle guide and to connect the needle guide to the cylindrical housing 104. Additionally, the frame 304 can be used with the alignment feature 128 to position the needle guide 110 and the needles 114 with respect to the imaging plane 208, as described above. In this example, the frame 304 is disposed within a negative alignment feature to position and align the needle 114A with the imaging plane 208 as described above. The needle housing 308, connected to the frame 304 and positioned within a second negative feature molded into the cylindrical housing 104 positions and aligns each of the needles 114 with the imaging plane 208 as described above.

The positioning feature 312 is connected to the frame 304 and is used to more firmly position the needle guide 110 in the alignment feature 128 by limiting movement of the frame within the alignment feature in additional directions. This reduces unintentional movement of the needle guide 110, thereby reducing risk of misalignment between the needles 114A-C and the imaging plane 208. In addition to reducing this risk of unintentional movement, the positioning feature 312 can enable more precise alignment of the needles 114A-C with the imaging plane 208. In this example, the positioning feature 312 is approximately orthogonal to an edge of the frame 304, thereby limiting movement of the frame in a direction parallel to the edge of the frame.

Other designs of positioning features can be used to reduce unintentional shifting of the frame 304, and therefore the needle guide 110, or improve alignment of the needles 114A-C with the imaging plane 208. In one example, the needle guide 110 is attached, fixed, or otherwise connected to the housing 308 using a clamp. In another example, the needle guide 110 is attached, fixed, or otherwise connected to the housing 308 using an elastic band that is properly positioned using a band guide groove in the needle guide and in the housing. Other types of clamps may also be used.

Also, while the needle guide 110 includes multiple channels 112 and can accommodate more than one needle 114 at a time, other examples include a single channel 112 and/or a single needle 114.

Summary

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. An ultrasonic probe comprising:
   a probe housing having a proximal end, a distal end, and a longitudinal axis;
   an ultrasonic transducer array disposed within the distal end of the housing, the ultrasonic transducer array being configured to produce a plurality of ultrasonic waves that form an ultrasonic imaging plane, having a frequency distribution centered at about 20 MHz;
   a needle guide;
   a protective sheath; and
   a needle guide alignment feature being a positive and/or negative feature disposed on a surface of the probe housing, wherein the needle guide alignment feature is configured to secure the needle guide to the probe housing with the protective sheath therebetween by mating with an approximately matching negative and/or positive feature on the needle guide, wherein the needle guide is arranged to guide a needle within the ultrasonic imaging plane when the needle guide is attached to the probe housing and wherein the needle guide alignment feature is configured to maintain alignment of the needle with the ultrasonic imaging plane.

2. The ultrasonic probe of claim 1, wherein the needle guide comprises at least two channels configured to guide needles translated through the channels at two different angles with respect to the longitudinal axis of the probe housing.

3. The ultrasonic probe of claim 2 wherein the needle guide further comprises:
   a port;
   a frame;
   a needle housing; and
   a positioning feature connected to the frame and configured to limit movement of the frame within the alignment feature in additional directions.

4. The ultrasonic probe of claim 3 wherein the frame includes an edge approximately orthogonal to the positioning feature, and wherein the movement of the frame is limited to movement in a direction parallel to the edge of the frame.

5. The ultrasonic probe of claim 2 wherein the needle guide is further configured to orient the needle substantially parallel to the longitudinal axis of the probe housing.

6. The ultrasonic probe of claim 1, wherein a dimensional variation of the alignment feature, a dimensional variation of the needle guide, and a dimensional variation of the protective sheath total about 250 microns.

7. The ultrasonic probe of claim 1, wherein the distal end comprises a face angled with respect to the longitudinal axis by at least 5° for acoustic coupling between the ultrasonic transducer array and a body structure.

8. The ultrasonic probe of claim 7, wherein the face is angled about 13° with respect to the longitudinal axis for acoustic coupling between the ultrasonic transducer array and a prostate.

9. The ultrasonic probe of claim 7 wherein the ultrasonic imaging plane formed by the transducer array is generally orthogonal to the face of the housing.

10. The ultrasonic probe of claim 1 wherein the ultrasonic imaging plane has a width of between about 300 and 500 microns.

11. The ultrasonic probe of claim 1, wherein the ultrasound transducer array is configured as a side-fire ultrasonic probe.

12. The ultrasonic probe of claim 1 wherein the ultrasonic imaging plane has a width, and wherein the needle guide is configured to receive a needle having a diameter greater than the width of the imaging plane.

13. The ultrasonic probe of claim 1 wherein the needle comprises a biopsy needle.

\* \* \* \* \*